(12) United States Patent
Zinser et al.

(10) Patent No.: US 11,905,296 B2
(45) Date of Patent: Feb. 20, 2024

(54) PROCESS FOR THE SYNTHESIS OF BUPRENORPHINE

(71) Applicant: AZAD PHARMA AG, Schaffhausen (CH)

(72) Inventors: Hartmut Zinser, Schaffhausen (CH); Tamar Danielyan, Abovyan (AM); Meri Grigoryan, Yerevan (AM); Mariam Gharibyan, Yerevan (AM); Mikayel Movsisyan, Yerevan (AM); Kristine Nerkararyan, Yerevan (AM)

(73) Assignee: AZAD PHARMA AG, Schaffhausen (CH)

( * ) Notice: Subject to any disclaimer, the term of this patent is extended or adjusted under 35 U.S.C. 154(b) by 0 days.

(21) Appl. No.: 17/790,042

(22) PCT Filed: Jan. 27, 2021

(86) PCT No.: PCT/EP2021/051785
§ 371 (c)(1),
(2) Date: Jun. 29, 2022

(87) PCT Pub. No.: WO2021/151908
PCT Pub. Date: Aug. 5, 2021

(65) Prior Publication Data
US 2023/0071914 A1    Mar. 9, 2023

(30) Foreign Application Priority Data

Jan. 27, 2020 (GB) ..................................... 2001121

(51) Int. Cl.
| | | |
|---|---|---|
| *C07D 489/12* | (2006.01) | |
| *C07B 49/00* | (2006.01) | |
| *C07B 43/08* | (2006.01) | |
| *C07B 43/04* | (2006.01) | |
| *C07B 31/00* | (2006.01) | |
| *C07B 37/12* | (2006.01) | |
| *C07D 498/12* | (2006.01) | |
| *A61P 25/36* | (2006.01) | |
| *A61P 25/04* | (2006.01) | |

(52) U.S. Cl.
CPC ............ *C07D 489/12* (2013.01); *A61P 25/04* (2018.01); *A61P 25/36* (2018.01); *C07B 31/00* (2013.01); *C07B 37/12* (2013.01); *C07B 43/04* (2013.01); *C07B 43/08* (2013.01); *C07B 49/00* (2013.01); *C07D 498/12* (2013.01)

(58) Field of Classification Search
CPC ........................... C07D 489/12; C07D 498/12
See application file for complete search history.

(56) References Cited

U.S. PATENT DOCUMENTS 9,624,231 B2    4/2017    Archer et al.

FOREIGN PATENT DOCUMENTS

| EP | 2813507 A1 | 12/2014 |
| WO | 2010039220 A1 | 4/2010 |
| WO | 2013050748 A2 | 4/2013 |

*Primary Examiner* — Susanna Moore
(74) *Attorney, Agent, or Firm* — Harness, Dickey & Pierce, P.L.C.

(57) ABSTRACT

The present invention relates to a novel route of synthesis for the opioid receptor antagonist Buprenorphine or a pharmaceutically acceptable salt thereof, starting from thebaine, wherein the route comprises the reaction of thebaine with a dienophile; forming an alkylated reaction product by reaction with a Grignard-reagent; formation of an cyanamide; deprotection of the cyanamide- and the phenolic-oxygenmoiety, wherein the cleavage of one or both groups is performed in the presence of an alkali or alkaline earth sulfide; followed by derivatization with a cyclopropyl-halogen and hydrogenation to yield Buprenorphine.

15 Claims, 1 Drawing Sheet

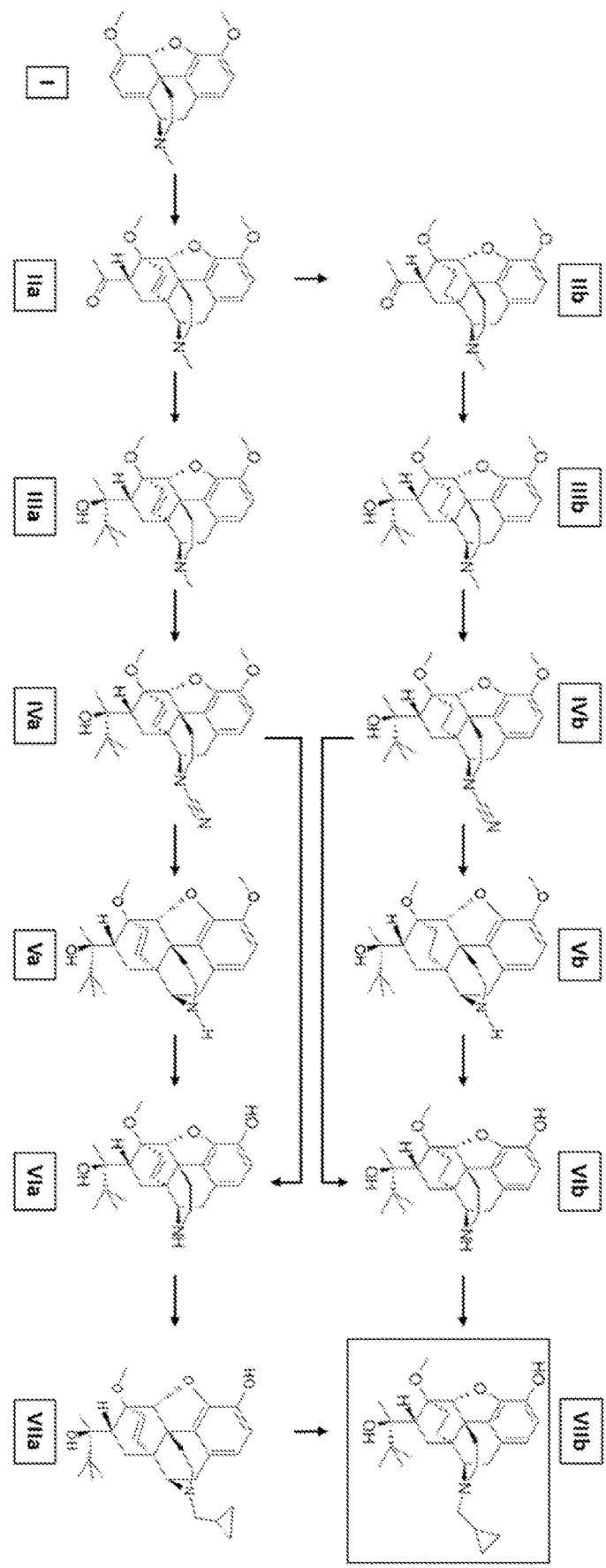

PROCESS FOR THE SYNTHESIS OF BUPRENORPHINE

CROSS-REFERENCE TO RELATED APPLICATIONS

This application is a U.S. National Phase Application under 35 U.S.C. 371 of International Application No. PCT/EP2021/051785, filed on Jan. 27, 2021, which claims the benefit of Great Britain Patent Application No. 2001121.9, filed on Jan. 27, 2020. The entire disclosures of the above applications are incorporated herein by reference.

FIELD OF THE INVENTION

The present invention relates to a novel route of synthesis for the opioid receptor antagonist Buprenorphine or a pharmaceutically acceptable salt thereof, starting from thebaine, wherein the route comprises the reaction of thebaine with a dienophile; forming an alkylated reaction product by reaction with a Grignard-reagent; formation of an cyanamide; deprotection of the cyanamide- and the phenolic-oxygen-moiety, wherein the cleavage of one or both groups is performed in the presence of an alkali or alkaline earth sulfide; followed by derivatization with a cyclopropyl-halogen and hydrogenation to yield Buprenorphine.

BACKGROUND

All medicinal opiate agents in use today are derived from naturally occurring morphine alkaloids by a multi-step semi-synthesis. Buprenorphine according to the following formula

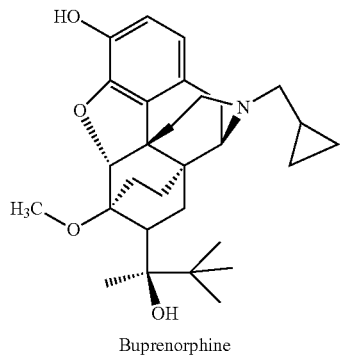 [SMILES: CO[C@]12CC[C@@]3(CC1[C@](C)(O)C(C)(C)C)[C@H]1Cc4ccc(O)c5c4[C@@]3(CCN1CC1CC1)[C@H]2O5]

Buprenorphine belongs also to the class of semisynthetic opiates and the compound is medicinally used as an analgesic, indicated for the treatment of moderate to severe pain and opioid dependence. A promising starting point for the synthesis of Buprenorphine is thebaine

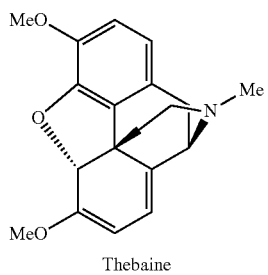 [SMILES: COC1=CC=C2[C@H]3Cc4ccc(OC)c5c4[C@@]2(CCN3C)[C@H]1O5]

Thebaine and several different routes of synthesis have been reported in the literature. Despite the numerous alternatives disclosed in the literature there still exist some drawbacks from the overall synthesis strategy, i.e. some of the necessary process steps suffer from the use of toxic reagents and laborious and yield diminishing multistep operations.

EP 2 813 507 A1 for instance discloses an industrial process for the preparation of 21-cyclopropyl-7a-(2-hydroxy-3,3-dimethyl-2-butyl)-6,14-endo-ethano-6,7,8,14-tetrahydro-oripavine, i.e. buprenorphine in high yield and purity, with enhanced safety and eco-friendly norms. The invention further relates to an improved process for preparation of intermediates thereof in high yield and purity.

In addition, U.S. Pat. No. 9,624,231 B2 also discloses a process for preparing buprenorphine and a method for increasing the yield of buprenorphine or a derivative thereof.

Nevertheless, besides the existing routes of synthesis there still exists the need for further high yield, non-toxic and eco-friendly routes of synthesis for Buprenorphine starting from thebaine.

DRAWINGS

FIG. 1 depicts a possible route of synthesis.

BRIEF DESCRIPTION OF THE INVENTION

Above mentioned problem is solved by a process for the synthesis of the opioid receptor antagonist Buprenorphine (5R,6R,7R,9R,13S,14S)-17-cyclopropylmethyl [(S)-3,3-dimethyl-2-hydroxybutan-2-yl]-6-methoxy-4,5-epoxy-6,14-ethanomorphinan-3-ol, or a pharmaceutical acceptable salt thereof, comprising the steps of a) reacting a thebaine-derivative according to the formula I and a dienophile to yield the reaction product II

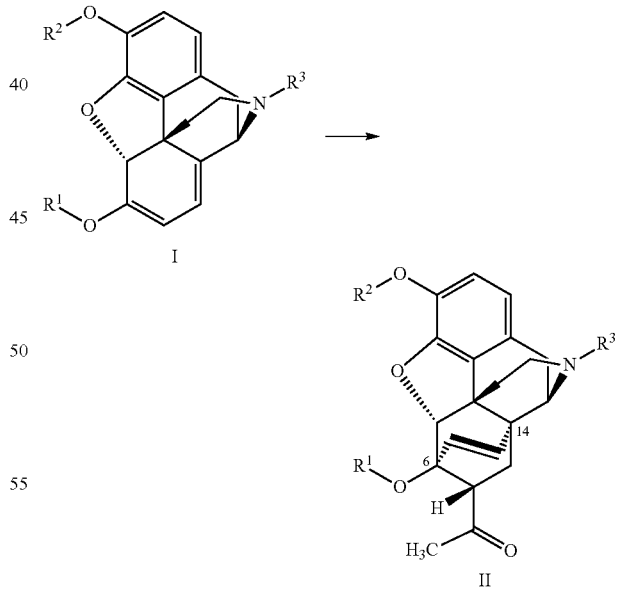

wherein, $R^1$, $R^2$ and $R^3$ are independently selected from the group consisting of H or C1-C3 alkyl and wherein the bridge between the 14 and the 6 position comprises one double or only single bonds;

b) contacting the reaction product II and a Grignard-reagent $R^4$—Mg—X to yield the corresponding alkylated reaction product according to the following formula III

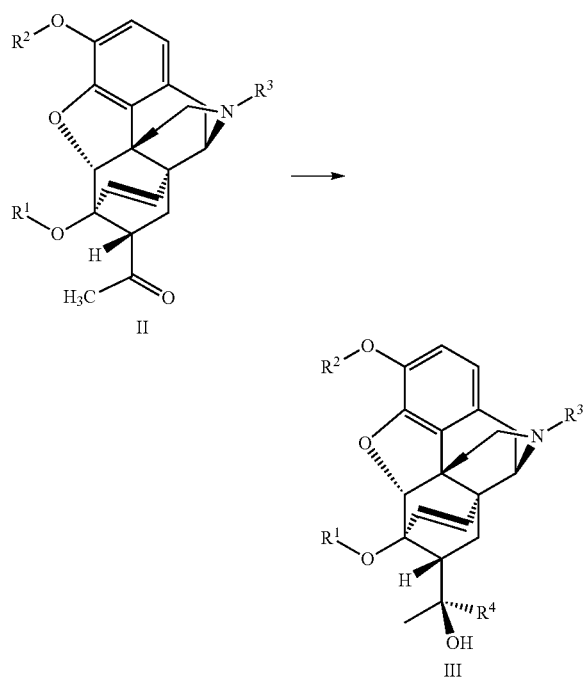

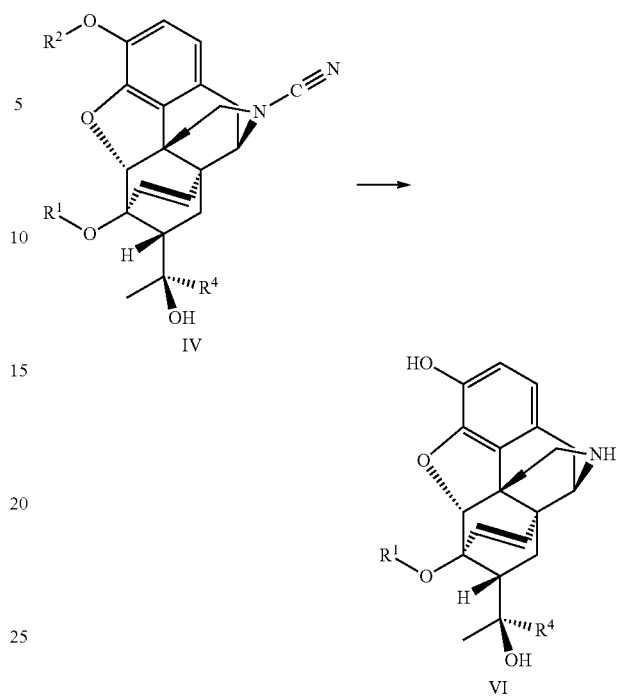

wherein R⁴ is selected from the group consisting of C1-C6-Alkyl and X is selected from the group consisting of I, Cl, F and Br;

c) reacting the compound according to formula III and a halo-cyanide to yield the corresponding cyanamide according to formula IV

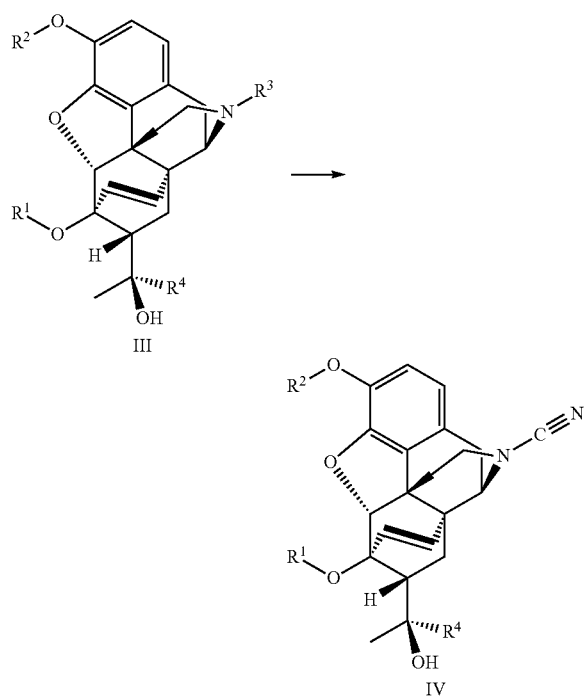

d) cleaving the cyanamide-moiety and the phenolic-oxygen-moiety to yield the deprotected intermediate according to formula VI e) derivatization of compound VI in the presence of a cyclopropyl-halogen and optionally hydrogenation of the bridge between C6 and C14 positions to comprise single bonds only to yield Buprenorphine, a Buprenorphine derivative or a Buprenorphine salt thereof,

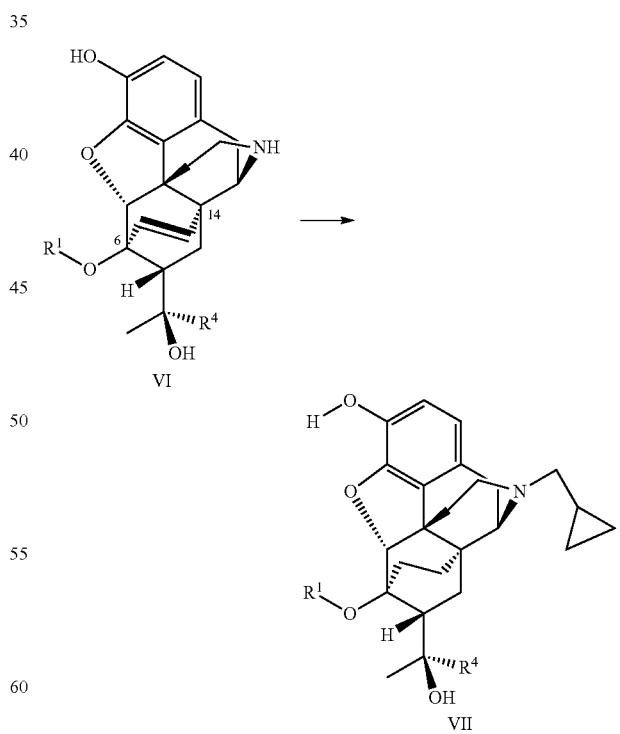

wherein at least one of the cleavages in step d) is performed in the presence of an alkali or alkaline earth sulfide. Surprisingly, it was found that the above depicted process is able to deliver Buprenorphine in high yields in short reaction times at moderate reaction conditions and therefore overall more economical process conditions. Especially, it has to be outlined that the cleavage step d) can be performed at much gentler reaction conditions compared to the state-of-the-art processes. Based on the better to handle and per se non-toxic reagents and the better process conditions in this step, lower amounts of un-wanted by-products are generated and, in addition, the by-products formation is better controllable, for instance compared to processes performing this step at higher temperatures and harsher reagents. Furthermore, it is even possible to perform this step in a one-pot reaction simultaneously for both protected moieties, resulting in a more streamlined synthesis comprising a lower amount and better controllable process steps compared to the state-of-the-art routes.

The inventive process is a process for the synthesis of the Buprenorphine or a pharmaceutical acceptable salt thereof. Therefore, the route of synthesis includes the specific preparation of Buprenorphine, but, as a function of pH, also the preparation of Buprenorphine salts comprising a charged Buprenorphine and pharmaceutically acceptable counter-ions are possible. In addition, the route of synthesis is flexible and different specific substitution patterns at the oxygens and the nitrogen are achievable by the inventive route of synthesis.

In process step a) a thebaine-derivative according to the formula I and a dienophile are reacted to yield the reaction product II

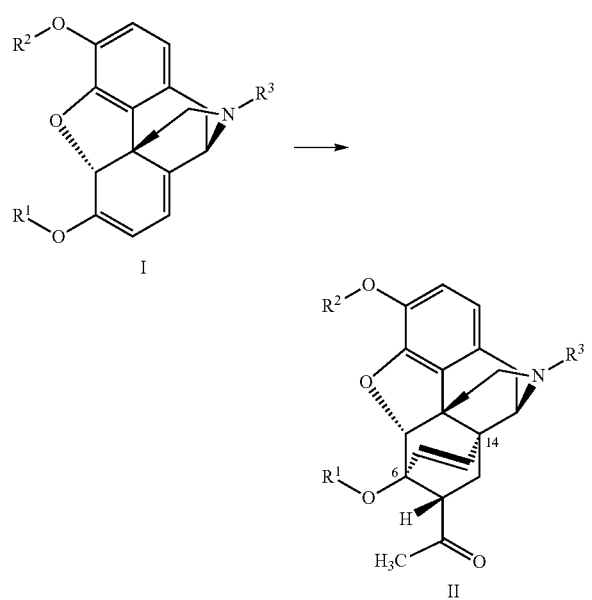

wherein, $R^1$, $R^2$ and $R^3$ are independently selected from the group consisting of H or C1-C3 alkyl and wherein the bridge between the 14 and the 6 position comprises one double or only single bonds. This conversion can be performed in two different ways, resulting in two different reaction products. Both reaction products can alternatively and equivalently be used in the further inventive process steps and this is the reason why both alternatives are displayed here. The reaction conditions at this conversion can be chosen in a way, that both thebaine double bonds are transformed into a bridge either comprising only alkyl or alkyl and one alkene double bond. A Diels-Alder type reaction results in the alkenyl, wherein subsequent hydrogenation results in the alkyl bridge. The hydrogenation to the alkyl-bridge can be performed in this process step or, alternatively, later on, in the course of the next process steps or at the very end of the synthesis. A suitable dienophile is for instance methylvinylketone. Other possibilities might include a multi-step reaction, wherein e.g. acrolein or acrylic acid (esters) are used in a first reaction, followed by additional process steps. However, based on the multi-step nature of this reaction step such alternatives are possible, but less preferred. The reaction can be performed in a temperature range from 50° C. up to 80° C. starting from 5 h up to 20 h.

In process step b) the reaction product II and a Grignard-reagent $R^4$—Mg—X are contacted to yield the corresponding alkylated reaction product according to the following formula III

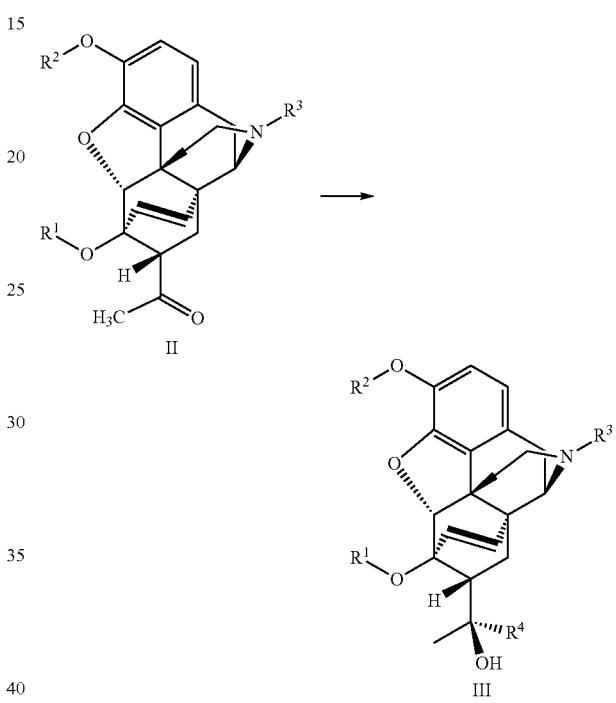

wherein $R^4$ is selected from the group consisting of C1-C6-Alkyl and X is selected from the group consisting of I, Cl, F and Br. The reaction can be performed in a temperature range from −10° C. up to 60° C. starting from 30 minutes up to 20 h. The reaction can be performed by commonly employed Grignard-solvents, for instance ethers, hydrocarbons or mixtures thereof.

In reaction step c) the compound according to formula III and a halo-cyanide are reacted to yield the corresponding cyanamide according to formula IV

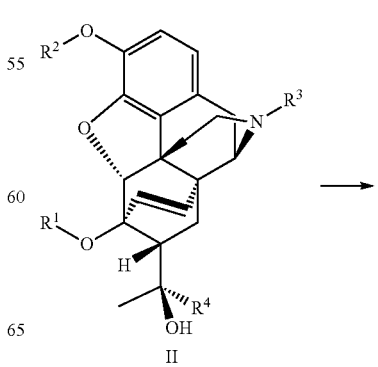

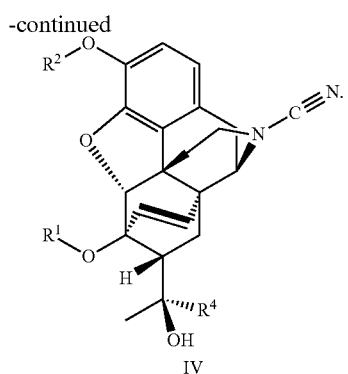

IV

The halogen of the halo-cyanide can be selected from the group of I, Cl, F and Br. The reaction can be performed in a temperature range from 20° C. up to 55° C. starting from 30 minutes up to 10 h. preferably the Br-cyanide can be used in this reaction step.

In reaction step d) the cyanamide-moiety and the phenolic-oxygen-moiety are cleaved to yield the deprotected intermediate according to formula VI

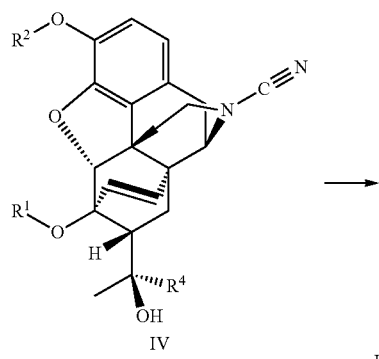

IV wherein at least one of the cleavages in step d) is performed in the presence of an alkali or alkaline earth sulfide. Suitable alkali sulfides can be selected from the group consisting of Li, Na, K, Rb or mixtures of at least two different sulfides thereof. Suitable alkaline earth sulfides can be selected from the group consisting of Mg, Ca, Sr or mixtures of at least two different sulfides thereof. In addition, it is possible to use mixed alkali/alkaline earth sulfides. This reaction can be performed in a one- or a two-step reaction. Literature examples affecting de-cyanation and O-Demethylation in one step hitherto feature the action of metalhydroxides in a protic solvent, e.g. KOH in diethylene glycol. The cyanamide cleavage typically can be affected at 110-130° C. and proceeds in good yields, whereas the de-methylation requires harsher conditions with temperatures exceeding 150° C. and reaction times of 24 h or more. The reported overall yields are moderate and not higher than 70%. The O-demethylation as a single reaction, e.g. as the last step in the sequence, is typically achieved by reaction of an alkyl- or arylthiolate in a dipolar-aprotic solvent, e.g. DMF or NMP, at typical temperatures of 120-130° C. and isolated yields of 80%-85% were reported. Combining the comparatively clean de-methylation reaction with sulfur-nucleophiles with the cyanamide cleavage employing metal hydroxides faces pronounced difficulties, because from the net equation, the cyanamide cleavage requires at least one molar equivalent of water in the presence of a strong base. None of the usual dipolar-aprotic solvents tolerates these conditions. For the O-demethylation—a $SN_2$ type reaction—dipolar-aprotic solvents are the ideal choice to maintain reactivity of the nucleophile. In protic solvents the reactivity of the nucleophile is significantly diminished. Those contradictory demands could surprisingly be reconciled by switching to an alkali/alkaline earth sulfide system, the $Na_2S$ hydrate system, especially. The $Na_2S$ may be utilized in various hydrated forms (e.g. tri-hydrate to nona-hydrate), providing the necessary molar quantities of water as reagent. In addition, the reagent is already a highly basic compound. Therefore, no additional base is needed in the step. In the course of the reaction the water content drops, rendering the sulfide even more reactive. As both, solvent and reagent, are highly water soluble, the isolation of product can easily be achieved by addition of water and adjustment of the pH to 10. In addition, regarding the price, this reaction is also very cost efficient.

In reaction step e) compound VI is derivatized in the presence of a cyclopropyl-halogen and optionally hydrogenation of the bridge between the 6 and the 14 position to comprise only single bonds to yield Buprenorphine, a Buprenorphine derivative or a Buprenorphine salt

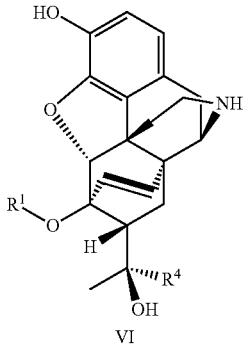

VI

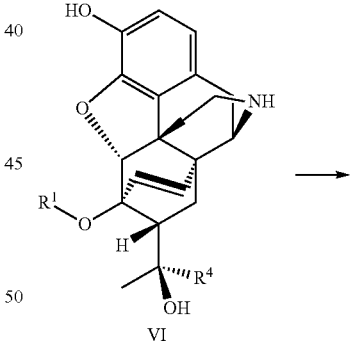

VI

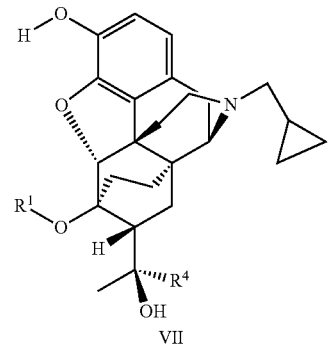

VII

The last part of the sequence consists of either one or two chemical transformations. On the one hand it is essential to attach an alkyl-moiety to the nitrogen. Furthermore, if not performed in a previous process step, the double bound has to be hydrogenated in order to achieve a pure alkyl-bridge. As already explained above, this second process step could have been performed independently in any of the prior mentioned process steps or at this stage. The substituent $R^1$ can be methyl and, consequently, in this case Buprenorphine is synthesized. By alteration of $R^1$ also other buprenorphine derivatives are achievable according to the inventive process. Typically, this alkylation reaction can be performed with the corresponding alkyl halides (Cl, Br, I) in a dipolar-aprotic solvent (mostly DMF). In addition, a scavenger for the released halide acid like $Na_2CO_3$ or diisopopylethylamine at elevated temperatures can be used.

In a preferred embodiment of the process in step d) the cleavage of the cyanamide-moiety and the phenolic-oxygen-moiety can be performed in the presence of an alkali or alkaline earth sulfide. With respect to the reaction efficiency it has been found very favorable, that the cyanamide-moiety and the phenolic-oxygen-moiety both can be cleaved using sodium sulfide as reagent. This reaction can either be performed in a step-wise fashion, by running the reaction under different temperature profiles in a one-pot reaction. It is also possible, that the reaction is performed using the same or different sodium sulfide reagents in a two-pot reaction. Therefore, besides using the same reagent for cleavage of the different protection groups, it is also possible that in a one or two-pot reaction different reaction conditions and sodium sulfide reagents are used for deprotection of the two moieties.

Within a further preferred embodiment of the process in step d) the cleavage of the cyanamide-moiety and the phenolic-oxygen-moiety can be performed in a one-pot reaction. Surprisingly, the cleavage can be performed at high yields and with very low amounts of unwanted by-products for both moieties in only one reaction solution and at the same reaction conditions. This is surprising, because based on the prior art it seemed not probable, that one reagent and one set of reaction conditions is able to provide the right chemical surrounding to cleave both protective groups without leading to other or further un-wanted by-products and low yields.

Within a further preferred embodiment of the process in step d) the cleavage is performed in the presence of $Na_2S*Z\ H_2O$, wherein Z=1-9. It has been found, that the hydration or crystal water in the sodium sulfide is an active component in the reaction and this given water content is promoting the cleavage of the protecting groups. Therefore, higher yields are obtainable at lower process times and less harsh reaction conditions.

In another preferred aspect of the process in step d) the cleavage can be performed in the presence of $Na_2S*Z\ H_2O$, wherein Z=3, 4, 5. It has been found, that the hydration or crystal water in the sodium sulfide is an active component in the reaction and this special water content is promoting the cleavage of the protecting groups. Therefore, higher yields are obtainable at lower process times and less harsh reaction conditions.

Within a further preferred embodiment of the reaction in step d) the cleavage of the cyanamide-moiety and the phenolic-oxygen-moiety can be performed in the presence of an alkali halide. For the overall reaction it has been found useful, that besides sodium sulfide as is, the reaction can be performed using a mixture of different alkali, e.g. potassium and/or lithium and sodium, sulfides. The different sulfides can be generated in situ by addition of the corresponding alkali halides via an in situ metathesis reaction. Such mixed systems are able to improve the yield at shorter reaction times. In addition, such metathesis reaction may save costs, because high quality lithium and potassium sulfides are accessible by such reaction.

In another preferred aspect of the process in step d) the cleavage can be performed in the presence of a protic polyamine solvent dipolar protic. It was found, that especially protic polyamine solvents are able to deliver, in combination with the inventively used alkali or alkaline earth sulfide, high yield cleavage of both protective groups even in one-pot reactions. Suitable dipolar protic solvents can for instance be selected from the group consisting of ethylenediamine, triethylenetetraamin, diethylene triamine (DETA), the corresponding partially N-methylated derivatives or mixtures of at least two solvents thereof. Furthermore, it was found that this type of solvents favorably combines the dissolution power of dipolar aprotic solvents without comprising the chemical stability, thereof.

Within a further preferred embodiment of the process in step d) the cleavage can be performed in the presence of Diethylene triamine (DETA) as solvent. The combination of the sodium sulfide and DETA as solvent has been found very favorable with respect to yield and by-product formation. Without being bound by the theory, it is believed that although DETA ranks among the protic solvents, its proton mobility is sufficiently decreased, as compared to alcohols, to maintain the nucleophiles reactivity and that DETA displays a high dissolution power for salts and is stable under the reaction conditions. These factors allow, in combination with the sodium sulfide, very favorable conditions in the course of a one-pot reaction to cleave both protective groups.

In a further preferred embodiment of the process in step d) the cleavage can be performed in the absence of further inorganic or organic bases. It was found that using alkali or alkaline earth sulfides as the sole base in the cleavage reaction reduces the complexity of the reaction, is able to provide high yields at short reaction times and is able to reduce the amount of un-wanted by products.

Within another preferred embodiment of the process in step d) the cleavage can be performed at a temperature of larger or equal to 100° C. and lower or equal to 160° C. This temperature range results in high yields of the double-deprotected compound at rather high reaction rates. Furthermore, the amount of un-wanted by-products is rather low. The latter can presumably be attributed to the less harsh reaction conditions compared to the state-of-the-art syntheses. In a further preferred embodiment of the invention the process step d) can be performed in a one pot reaction at a temperature of larger or equal to 110° C. and lower or equal to 150° C., further preferred of larger or equal to 120° C. and lower or equal to 140° C. Such temperature ranges further enhance the selectivity of the reaction at very acceptable reaction rates.

In a further preferred embodiment of the process in step d) the molar ratio of the compound according to formula IV and alkali or alkaline earth sulfide, calculated as compound (IV) divided by alkali or alkaline earth sulfide, is larger or equal 0.1 and smaller or equal 1.0. It was found that above given molar ratio between the substrate compound IV and the sulfide results in a very specific de-protection reaction by cleavage of the protective alkyl groups at the nitrogen and the oxygen. This reaction can furthermore be performed as a one pot reaction in the same reaction media at the same reaction conditions. This might result in a less complicated course of reaction and lower losses based on laborious in-between cleaning operations. Further preferred is a molar ratio of larger or equal 0.25 and smaller or equal 0.4, and even further preferred of larger or equal 0.25 and smaller or equal 0.35.

In a further preferred aspect of the process the molar concentration of the compound according to formula IV in the solvent of the process step d) can be larger or equal to 0.25 mol/L and smaller or equal to 1.5 mol/L. This absolute concentration of the substrate in the reaction solvent is able to establish high capacities for a high-throughput process and increases the economic use of vessel/equipment. The concentration range can be established without the risk of reducing the overall yield by increasing the build-up of unwanted side-products.

Within a preferred characteristic of the process the reaction time in step d) can be larger or equal to 10 h and smaller or equal to 20. Based on the proposed reaction step a better time efficiency can be obtained, resulting in lower costs.

In a further preferred aspect of the process the reaction mixture in process step d) can be diluted with aqueous NaOH followed by washing with 2-methoxy-2-methylpropane (MTBE) after the reaction is finished. It has been found suitable, that the reaction mixture after process step d) is subjected to a treatment removing any unconverted intermediate from the reaction mixture. This object is readily achieved by adding aqueous sodium hydroxide to the reaction mixture and washing the combined mixture one or more times with MTBE. Optional the unreacted intermediate can be recycled by collecting the MTBE layers and feeding the isolated intermediate back into the process. It was surprisingly found that MTBE is able to isolate the intermediate in a purity of >98% (area % HPLC), eliminating more complicated cleaning or purification steps.

In another preferred aspect of the process in reaction step d) the molar conversion of compound IV to compound V can be larger or equal 90% and smaller or equal 95%. It has surprisingly been found, that the selectivity and output of this reaction step is best in cases, wherein the reaction is not pushed to completion but stopped at a conversion of the intermediate of 90-95%. Although more product could theoretically be synthesized in this reaction step, this limited conversion of compound IV comprises better results, because a lower amount of un-wanted side-products is generated and the recuperated intermediate can be recycled.

In a further preferred embodiment of the process in reaction step e) compound VI can be isolated by crystallization started by addition of saturated NH$_4$Cl-solution or hydrochloric acid at temperatures of larger or equal to 50° C. and smaller or equal to 60° C., followed by cooling of the mixture. Within this crystallization a very clean product can be obtained without significant product losses. The isolation yield is in excess of 90% and even more in the range of 95% of the total of formed product. The purities can be in the range of larger than 98.0% up to 99.0%; which is sufficiently pure for the next synthesis step, obviating the need for further purification.

Within a preferred embodiment the non-converted intermediates in each reaction step can be recycled and submitted to the same reaction conditions within another reaction cycle again. Such process is feasible, either by introduction of the isolated material in the same reaction step again or by performing a single batch with the collected recuperated material, e.g. at the end of a production campaign. Such recycling is able to safe costs and energy and reduces the CO$_2$ burden of the overall synthesis. It is in no way obvious that such recycling can be performed, because in the synthesis of drugs usually such recycling is not preferred, because of the possible accumulation of un-wanted side-products. Preferably, the recycling is performed in each step.

EXPERIMENTAL EXAMPLES

I. Reaction Step a)

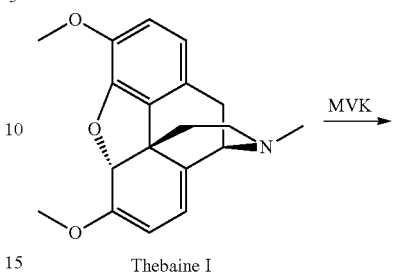

Thebaine I

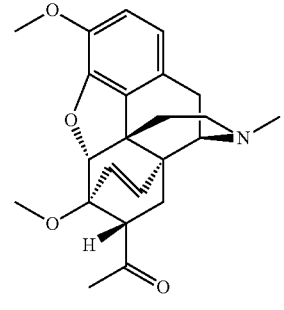

α-Thevinone IIa

To a mixture of Compound I (Thebaine, 20.0 g, 64.23 mmol), isopropanol (28 g) and water (14 g), Methyl vinyl ketone (MVK, 13.51 g, 192.69 mmol, 3.0 eq) was added at ambient temperature. The suspension was heated to 60° C. After 16 h of stirring at 60° C. the reaction was complete and the suspension was cooled to 50° C. A second portion of water (14 g) was added and the suspension cooled to 0-5° C. The product was filtered off, the wet cake was washed with water and dried in vacuum at 40° C. to afford 22.63 g of Compound IIa (92.3% yield) as an off-white solid with an HPLC purity of 99.3%.

II. Optional Hydrogenation of Compound II

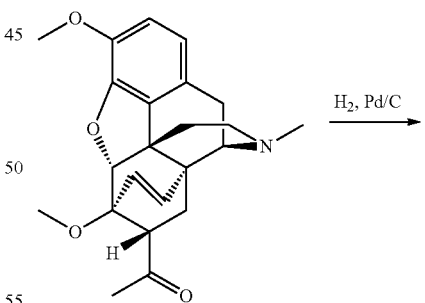

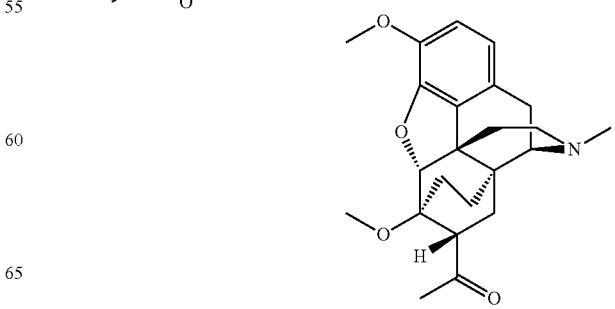

Compound IIa (10 g, 26.215 mmol) was dissolved in a mixture of acetic acid (3 g) and water (100 g). 5% Pd on Carbon (wet) was added and the mixture was hydrogenated at 3 bar of hydrogen pressure at ambient temperature. The progress of the hydrogenation reaction was monitored by HPLC. After 18 h the reaction was complete. The catalyst was removed by filtration, and the pH of the filtrate was adjusted to 10 by adding 40% sodium hydroxide solution. Precipitated solid was filtered off, the filter cake was washed with water and dried in vacuum at 40° C. to afford 9.5 g of hydrogenated Compound IIb (94.5% yield) as an off-white solid with an HPLC purity of 99.8%.

III. Reaction Step b)

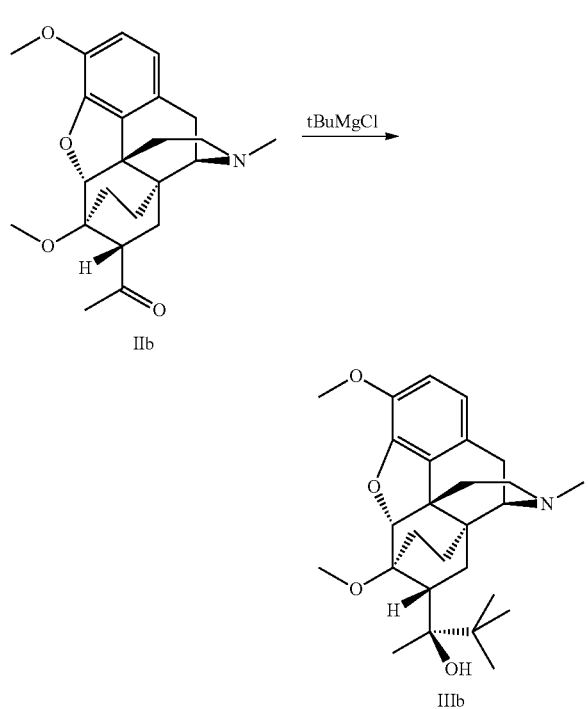

To a mixture of tert-Butyl magnesium chloride 1.7 M solution in diethyl ether (92.0 mL, 156.5 mmol) and toluene (50 mL), diglyme (15.8 g, 117.3 mmol) was added slowly at 0-5° C. A solution of hydrogenated Compound IIb (10.0 g, 26.1 mmol) in 1:1 toluene/diethyl ether (60 mL) was added dropwise to the Grignard reagent, maintaining internal temperature in the range of 2-5° C. The mixture was stirred for an additional hour at 0-5° C. The reaction mixture was quenched with a mixture of acetone and diethyl ether, maintaining the internal temperature below 20° C., followed by addition of a saturated aqueous ammonium chloride solution. Phases were separated and the organic layer was washed with water, followed by brine. The organic layer was concentrated and the solvent gradually replaced by Ethanol (70 mL) and water (15 mL). The mixture was stirred under reflux for 2 h, then cooled gradually to 0-5° C. Crystallized solid was collected by filtration, and dried in vacuum to afford 9.1 g of Compound IIIb (79% yield) as a white solid with an HPLC purity of 99.0%.

III. Reaction Step b)—Directly from Compound IIa, No Hydrogenation

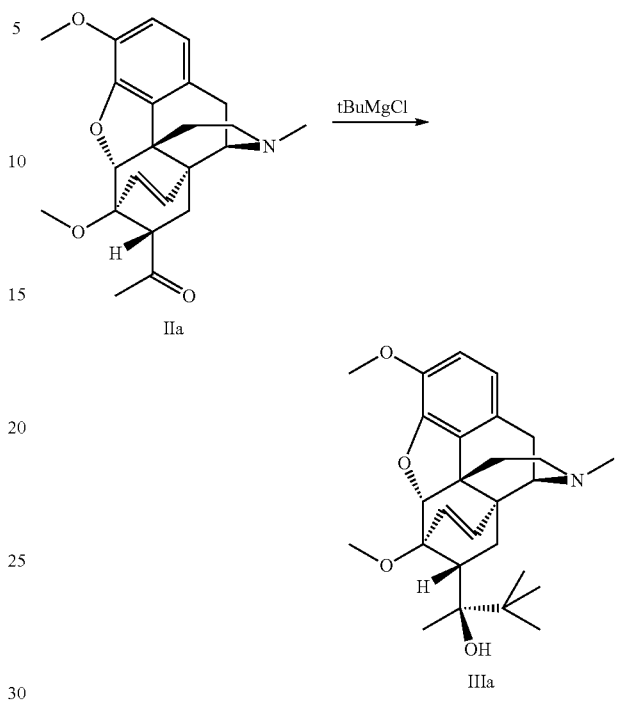

A solution of tert-Butyl magnesium chloride 1.7 M solution in diethyl ether (92.5 mL, 157.3 mmol) was diluted with toluene (70 mL) and cooled to 5° C. Diglyme (14.35 g, 106.9 mmol) was added slowly at 5-10° C. A solution of Compound IIa (10.0 g, 26.2 mmol) in a 1:1 (w/w) toluene/diethyl ether mixture (75 mL) was added dropwise to the above mixture, maintaining internal temperature in the range of 0-5° C. Stirring was continued at 5° C. for 1.5 h. The reaction was quenched with a solution of acetone in diethyl ether, followed by the addition of a saturated ammonium chloride solution. Phases were separated and the organic layer was washed with water. The toluene/ether solvent was evaporated and gradually replaced by ethanol (150 mL). The solution was heated under reflux for an hour, water (36 mL) was added, refluxed for another hour and allowed to cool to 5° C. Precipitated solid was filtered off, the product was washed with EtOH/water 1:1 mixture and dried in vacuum to afford 9.56 g of Compound IIIa (83% yield) as a white solid with an HPLC purity of 99.8%.

IV. Reaction Step c) on the Hydrogenated Form of Compound III

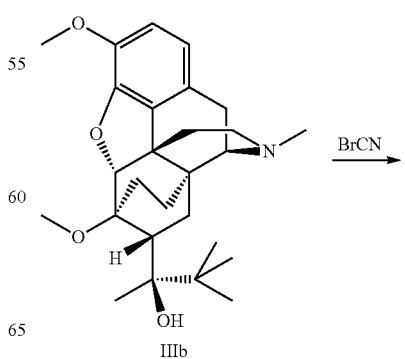

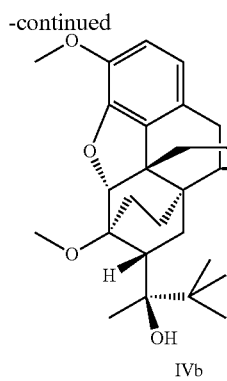

IVb

To a suspension of Compound IIIb (10.0 g, 22.6 mmol) and potassium carbonate (1.65 g, 11.93 mmol) in acetonitrile (40 mL), cyanogen bromide 3 M solution in DCM (10.5 mL, 31.6 mmol) was added dropwise at ambient temperature, then heated to 40° C. and stirred for 6 h. The reaction mixture was concentrated to ⅓ of the initial volume, then water (50 mL) was added. Precipitated material was filtered off, the wet cake was washed with water and dried in vacuum at 50° C. to afford 10.8 g of Compound IVb (quant.) as a white solid with an HPLC purity of 99.3%.

IV. Reaction Step c) on the Non-Hydrogenated Form of Compound III

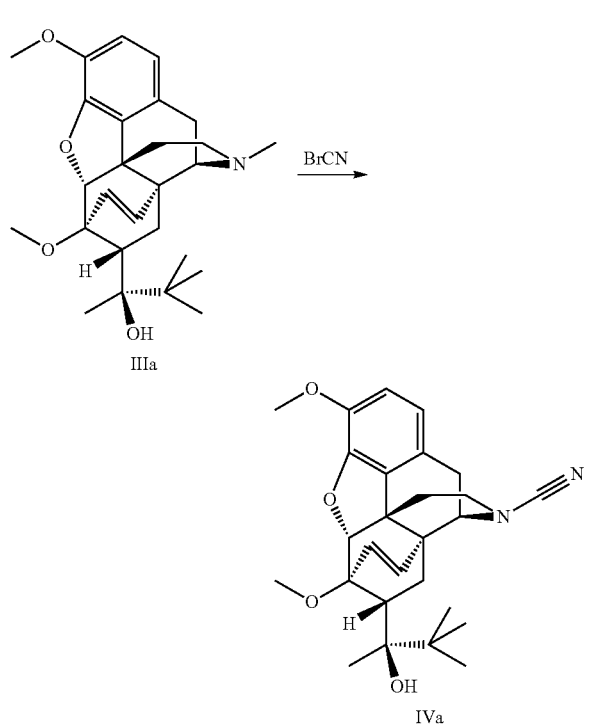

IIIa

IVa

To a suspension of Compound IIIa (10.0 g, 22.7 mmol) and potassium carbonate (1.57 g, 11.4 mmol) in acetonitrile (35 mL), cyanogen bromide 3 M solution in DCM (10.5 mL, 31.6 mmol) was added dropwise at ambient temperature, then heated to 40° C. and stirred for 6 h. Reaction mixture was cooled to ambient temperature, water (1 mL) was added and DCM was evaporated. To the residue water (60 mL) was added and acetonitrile was distilled off azeotropically. Residue was cooled to ambient temperature, precipitated material was filtered off, wet cake was washed with water and dried in vacuum at 50° C. to afford 9.93 g of Compound IVa (98% yield) as a white solid with an HPLC purity of 99.5%.

IV. Reaction Step d)—Alternative I—Hydrogenated Substrate

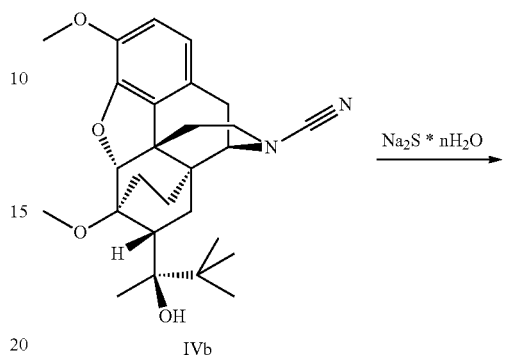

IVb

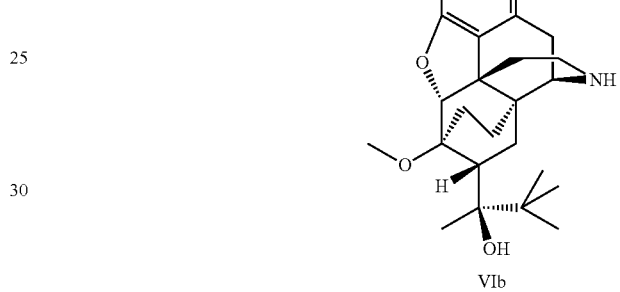

VIb

A mixture of Compound IVb (5.1 g, 11.3 mmol), sodium sulfide nonahydrate (8.2 g, 33.9 mmol) and DETA (15 mL) was added to a vessel and rendered inert. The suspension was first heated to 110° C., followed by a gradual heating (6 h) to 135° C., followed by increasing the temperature to 150° C. and stirring for 4 h. The mixture was cooled to 30° C. and 20 mL of NaOH 1 M solution was slowly added, followed by 20 mL of TBME. Layers were separated. The TBME layer contained 0.47 g of intermediate compound V, wherein only the deprotection at the nitrogen took place (98% purity). The aqueous layer was heated to 50° C. and 20 mL of sat. NH$_4$Cl solution were added slowly. The thick suspension was cooled to 20° C., stirred for 5 h and filtered. The filter cake was washed with water and TBME and dried under vacuum, leading to 3.88 g Compound VIb with a purity of 92.5%.

Na$_2$S*4 H$_2$O (dried from the nonahydrate at 40° C. under vacuum)

A mixture of Compound IVa (5.0 g, 11.1 mmol), sodium sulfide tetrahydrate (5.00 g, 33.3 mmol) and DETA (20 mL) was added to a vessel and rendered inert. The suspension was first heated to 110° C., followed by a gradual heating (6 h) to 135° C. At 135° C. the mixture was stirred for further 12 h. The mixture was cooled to 30° C. and 20 mL of NaOH 1 M solution was slowly added, followed by 20 mL of TBME. Layers were separated. The TBME layer was discarded. The aqueous layer was heated to 50° C. and 20 mL of sat. NH$_4$Cl solution were added slowly. The thick suspension was cooled to 20° C., stirred for 6 h and filtered. The filter cake was washed with water and TBME and dried under vacuum, leading to 3.36 g Compound VIa with a purity of 95.5%.

Compound VIa can optionally be further purified by suspending the isolated wet product in hot THF/water 9:1 or DMF/water 2:1.

V. Reaction Step d)—Alternative II—Non-Hydrogenated Substrate

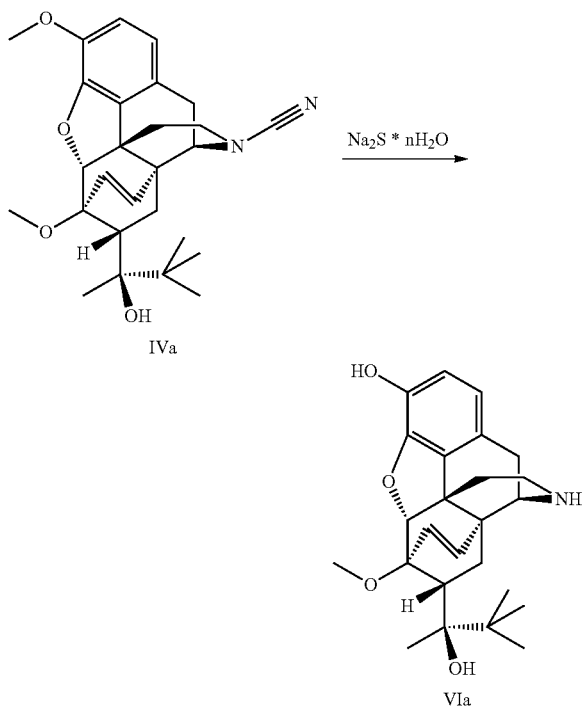

A mixture of Compound IVa (7.1 g, 15.8 mmol), sodium sulfide nonahydrate (13.3 g, 55.2 mmol) and DETA (35 mL) was added to a vessel and rendered inert. The suspension was heated to 130° C. within two hours and stirred for 21 h. The mixture was cooled to 30° C. and 25 mL of NaOH 1 M solution was slowly added. The mixture was filtered yielding 0.8 g of intermediate Compound Va (93% purity). To the filtrate 30 mL of TBME were added. Layers were separated. The aqueous layer was heated to 50° C. and 30 mL of sat. NH$_4$Cl solution were added slowly. The thick suspension was cooled to 20° C., stirred for 5 h and filtered. The filter cake was washed with water and TBME and dried under vacuum, leading to 4.48 g Compound VIa with a purity of 97.9%.

In addition, the reaction can be performed using Na$_2$S*3H$_2$O (aka Na$_2$S 60%).

A mixture of Compound IVa (4.51 g, 10.0 mmol), sodium sulfide trihydrate (5.28 g, 40.0 mmol) and DETA (30 mL) was added to a vessel and rendered inert. The suspension was heated to 140° C. within two hours and stirred for 22 h. The mixture was cooled to 40° C. and 30 mL of NaOH 1 M solution was slowly added. The mixture was stirred for 30 min, then clarified. To the filtrate 50 mL of TBME were added. Layers were separated. The aqueous layer was heated to 50° C. and 35 mL of 1.5 M HCl solution were added slowly. The thick suspension was cooled to 20° C., stirred for 5 h and filtered. The filter cake was washed with water and TBME and dried under vacuum, leading to 2.8 g Compound VIa with a purity of 99.1%.

The reaction with sodium sulfide trihydrate can also be performed in different solvents.

Compound IVa (2.02 g, 4.5 mmol), sodium sulfide trihydrate (2.07 g, 15.7 mmol) and Ethanolamine (14 mL) were added to a vessel and rendered inert. The suspension was heated to 130° C. within 1.5 hours and then to 140° C. within 0.5 h. Stirring was continued for stirred for 47 h. 8 ml of Ethanolamine were distilled off at an external temperature of 125° C.-127° C. Afterwards, the suspension was cooled to room temperature, 8 mL of water were added and the mixture was stirred for 14 h. The suspension was filtered, the filter cake washed with 5 mL water and the isolated material dried for 15 h at 50° C. under vacuum yielding 1 g of Compound VIa with a purity of 93%. The filtrate was cooled to 5° C. and the pH adjusted to 8.6 by addition of 14 mL of 6M HCl keeping the temperature between 5° C. and 10° C. The resulting suspension was stirred at this temperature for 2 h. The solids were filtered off and washed with 5 mL of water followed by 2×5 ml 2-propanol/water. After drying for 15 h at 50° C. under vacuum, additional 0.46 g of Compound VIa were obtained as beige powder with a purity of 91.8%.

Compound IVa (2.0 g, 4.4 mmol), sodium sulfide trihydrate (2.05 g, 15.5 mmol), Lithium chloride (1.45 g, 34.2 mmol) and Triethylenetetraamine (14 mL) were added to a vessel and rendered inert. The suspension was heated to 140° C. within 0.5 h and stirred for 19 h. The suspension was cooled to 70° C., 18.5 ml water were added and stirred for 1 h. The suspension was filtered at 70° C. and the filter cake washed three times with 3 mL of water. The filtrate was cooled to room temperature and 5.2 mL 6M HCl were added dropwise keeping the temperature below 35° C. forming a precipitate. Stirring at room temperature was continued for 1 h followed by filtration and washing of the filter cake two times with 3 mL of water. After drying for 15 h at 50° C. under vacuum, 1.53 g of Compound VIa were obtained as yellowish powder with a purity of 98.0%.

Compound IVa (2.0 g, 4.4 mmol), sodium sulfide trihydrate (2.05 g, 15.5 mmol) and Ethylenediamine (14 mL) were added to a vessel and rendered inert. The suspension was heated to reflux and kept at this condition for 64 h. The suspension was cooled to 70° C., 18.5 ml water were added and stirred for 1 h. The suspension was filtered at 70° C. and the filter cake washed three times with 3 mL of water. The filtrate was cooled to room temperature and 5.2 mL 6M HCl were added dropwise keeping the temperature below 35° C. forming a precipitate. Stirring at room temperature was continued for 1 h followed by filtration and washing of the filter cake two times with 3 mL of water. After drying for 15 h at 50° C. under vacuum, 0.94 g of Compound VIa were obtained as grey powder with a purity of 96.0%.

In addition, the reaction can be performed using Na$_2$S*3H$_2$O (Na$_2$S 60%) and LiCl A mixture of Compound IVa (2.0 g, 4.4 mmol), sodium sulfide trihydrate (2.34 g, 17.8 mmol), Lithium chloride (0.76 g, 17.8 mmol) and DETA (17 mL) was added to a vessel and rendered inert. The suspension was heated to 140° C. within two hours and stirred for 16 h. The mixture was cooled to 40° C. and 15 mL of NaOH 1 M solution was slowly added. The mixture was clarified. To the filtrate 20 mL of TBME were added. Layers were separated. The aqueous layer was heated to 50° C. and 7 mL of 5 M HCl were added slowly. The thick suspension was cooled to 20° C., stirred for 5 h and filtered. The filter cake was washed with water and TBME and dried under vacuum, leading to 1.34 g Compound VIa with a purity of 98.0%.

The Compound VIa can be re-worked. A preferred procedure may include:

1 g of Compound VIa not meeting the set purity requirements is dissolved in 4 g of DETA and 4 mL of 1 M NaOH at 60° C. Turbid solutions are clarified. Solution is slowly treated with 2 mL of 2 M HCl at 60° C., then allowed to cool to room temperature. The product is collected by filtration, washed with water and dried. Typical purity after re-work is >98.5% with a yield of 90-95%.

VI. Reaction Step e)—Alternative I—Hydrogenated Substrate

VII. Reaction Step e)—Alternative II—Non-Hydrogenated Substrate

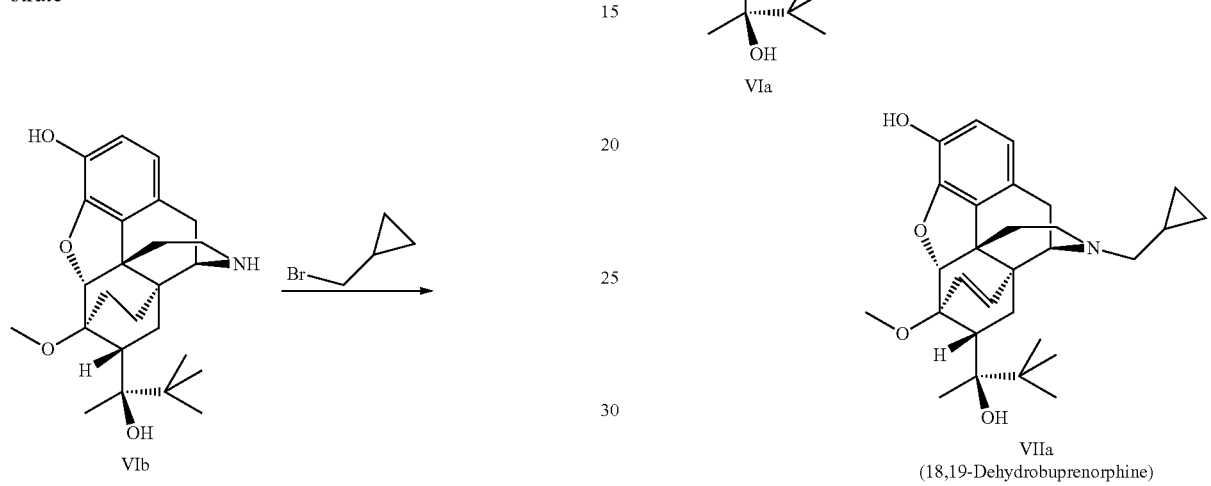

Compound VIa (3.0 g, 7.29 mmol) was suspended in 10 mL of DMF. 2.8 g DIPEA (21.9 mmol) and 1.48 g (10.9 mmol) Cyclopropyl methyl bromide were added and the suspension was heated to 70° C. The mixture was stirred for 12 h (>99.5% conversion), cooled to 50° C. and quenched with 1.27 mL (15 mmol) of 41% aq. Methylamine solution. Stirring was continued for 2 h, then cooled to ambient temperature. 10 mL of water were added dropwise, the resulting suspension was cooled to 5° C., filtered and washed with water. The wet product was recrystallized from EtOH/water (2:1 v/v). Compound VIIa (2.9 g, 85%) was isolated as off-white powder with a purity of 99.2%

Hydrogenation of Intermediate Compound VIIa

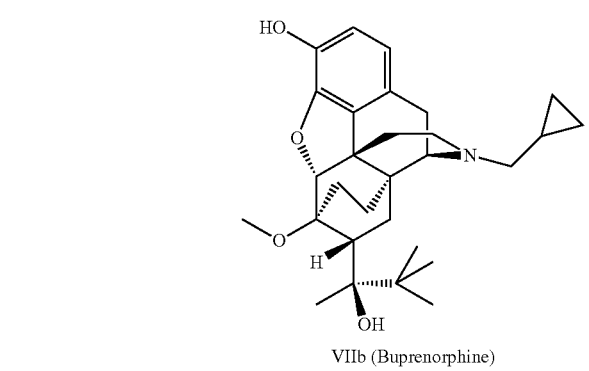

Compound VIb (2.0 g, 4.84 mmol) is dissolved in 10 mL of DMF. 1.9 g DIPEA (14.6 mmol) and 0.92 g (6.8 mmol) Cyclopropyl methyl bromide were added and the suspension was heated to 70° C. The mixture was stirred for 7 h (>99.5% conversion), cooled to 50° C. and quenched with 0.85 mL (10 mmol) of 41% aq. methylamine solution. Stirring was continued for 2 h, then cooled to room temperature. DMF was diluted with 20 mL of water and 10 mL of brine, followed by extraction with 20 mL of Me-THF. The organic layer was washed twice with water. The solvent was distilled off and the solid residue crystallized from toluene/c-hexane 1:1 (v/v). Compound VIIb (Buprenorphine, 1.95 g, 86%) was isolated as yellowish powder with a purity of 99.0%.

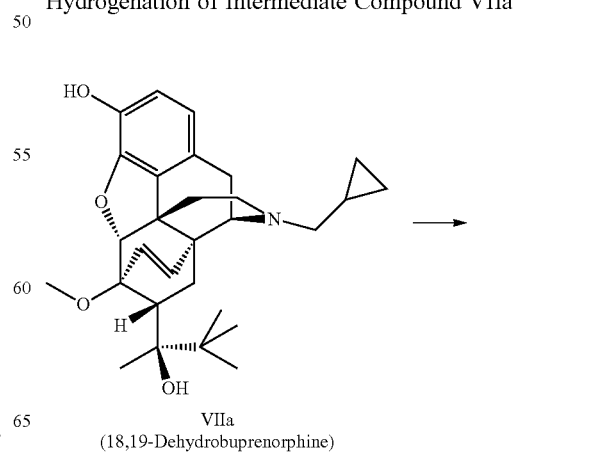

-continued

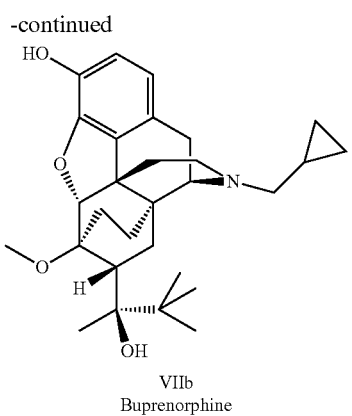

VIIb
Buprenorphine

Compound VIIa (1.98 g, 4.25 mmol) and 0.2 g 5% Pd/C (50%, wet) were suspended in 20 mL of EtOH, 1.5 g Acetic acid (6 eq) and 3 mL of water and hydrogenated at 45° C. and 5 bar pressure for 16 h. A second portion of catalyst was added and hydrogenation resumed for another 24 h. Catalyst was filtered and the mixture was partially evaporated. After addition of bicarbonate-solution the mixture was extracted with toluene. The toluene layer was concentrated and c-Hexane was added to result in a Toluene/c-Hexane 1:1 (v/v) mixture from which the product was crystallized. Isolation yielded 1.61 g (81%) Buprenorphine (Compound VIIb) with 99.2% purity.

What is claimed:

1. A process for the synthesis of the opioid receptor antagonist Buprenorphine (5R,6R,7R,9R,13S,14S)-17-Cyclopropylmethyl-7-[(S)-3,3-dimethyl-2-hydroxybutan-2-yl]-6-methoxy-4,5-epoxy-6,14-ethanomorphinan-3-ol, or a pharmaceutical acceptable salt thereof, comprising the steps of
   a) reacting a thebaine-derivative according to the formula I and a dienophile to yield the reaction product II

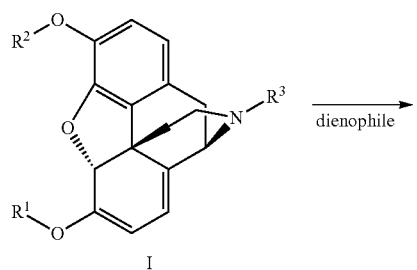

I wherein, $R^1$, $R^2$ and $R^3$ are independently selected from the group consisting of H or C1-C3 alkyl and wherein the bridge between the 14 and the 6 position consists of one double or only single bonds;
   b) contacting the reaction product II and a Grignard-reagent $R^4$—Mg—X to yield the corresponding alkylated reaction product according to the following formula III

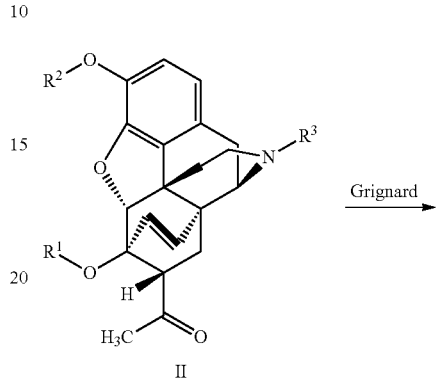

II

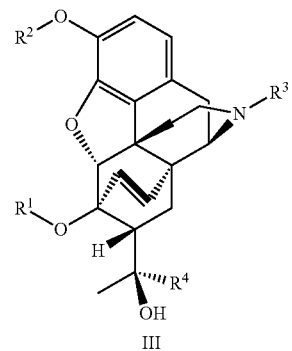

III wherein $R^4$ is selected from the group consisting of C1-C6-Alkyl and X is selected from the group consisting of I, Cl, F and Br;
   c) reacting the compound according to formula III and a halo-cyanide to yield the corresponding cyanamide according to formula IV

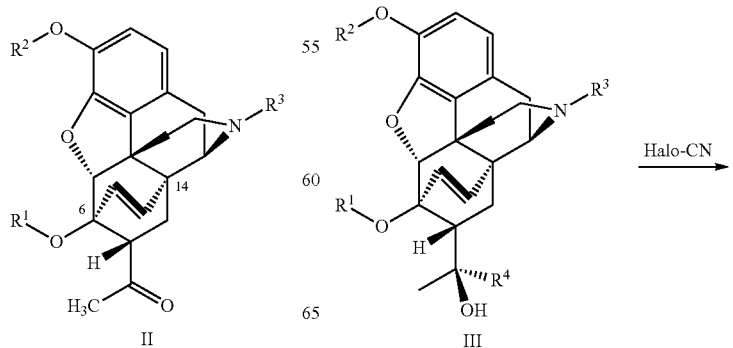

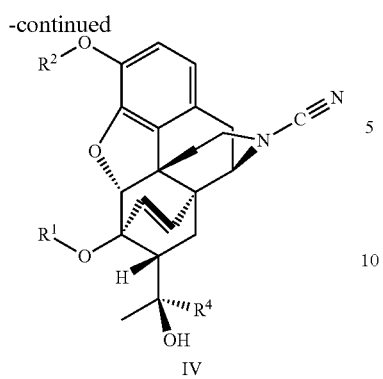

IV d) cleaving the cyanamide-moiety and the phenolic-oxygen-moiety to yield the deprotected intermediate according to formula VI

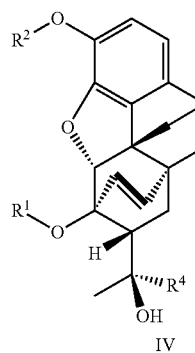

IV

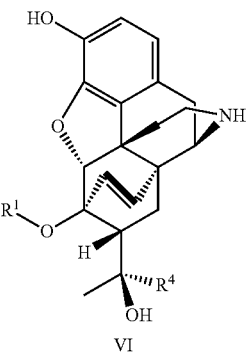

VI e) derivatization of compound VI in the presence of a cyclopropyl-methylene-halogen and optionally hydrogenation of the bridge between C6 and C14 positions to comprise single bonds only to yield Buprenorphine, a Buprenorphine derivative according to compound VII or a Buprenorphine salt

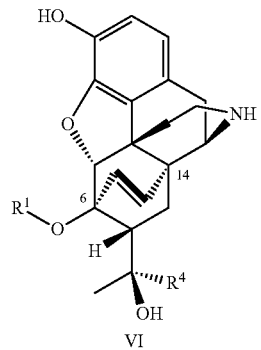

VI

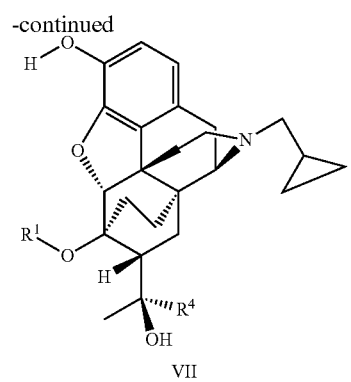

VII wherein at least one of the cleavages in step d) is performed in the presence of an alkali or alkaline earth sulfide.

2. The process according to claim 1, wherein in step d) the cleavage of the cyanamide-moiety and the phenolic-oxygen-moiety is performed in the presence of an alkali or alkaline earth sulfide.

3. The process according to claim 1, wherein in step d) the cleavage of the cyanamide-moiety and the phenolic-oxygen-moiety is performed in a one-pot reaction.

4. The process according to claim 1, wherein in step d) the cleavage is performed in the presence of $Na_2S*Z\ H_2O$, wherein Z=1-9.

5. The process according to claim 1, wherein in step d) the cleavage is performed in the presence of $Na_2S*Z\ H_2O$, wherein Z=3, 4, 5.

6. The process according to claim 1, wherein in step d) the cleavage of the cyanamide-moiety and the phenolic-oxygen-moiety is performed in the presence of an alkali halide.

7. The process according to claim 1, wherein in step d) the cleavage is performed in the presence of a protic polyamine solvent.

8. The process according to claim 1, wherein in step d) the cleavage is performed in the presence of Diethylene triamine (DETA) as solvent.

9. The process according to claim 1, wherein in step d) the cleavage is performed at a temperature of larger or equal to 100° C. and lower or equal to 160° C.

10. The process according to claim 1, wherein in step d) the molar ratio of the compound according to formula IV and alkali or alkaline earth sulfide, calculated as compound (IV) divided by alkali or alkaline earth sulfide, is larger or equal to 0.1 and smaller or equal to 1.0.

11. The process according to claim 1, wherein the molar concentration of the compound according to formula IV in the solvent of the process step d) is larger or equal to 0.25 mol/L and smaller or equal to 1.5 mol/L.

12. The process according to claim 1, wherein the reaction mixture in process step d) is diluted with aqueous NaOH followed by washing with 2-methoxy-2-methylpropane after the reaction is finished.

13. The process according to claim 1, wherein in reaction step d) the molar conversion of compound IV to compound V is larger or equal to 90% and smaller or equal to 95%.

14. The process according to claim 1, wherein in reaction step e) compound VI is isolated by crystallization started by addition of saturated $NH_4Cl$-solution or hydrochloric acid at temperatures of larger or equal to 50° C. and smaller or equal to 60° C., followed by cooling of the mixture.

15. The process according to claim 1, wherein in step d) the cleavage is performed in the absence of further inorganic or organic bases.

\* \* \* \* \*